US010435750B2

(12) United States Patent
Goossens et al.

(10) Patent No.: US 10,435,750 B2
(45) Date of Patent: Oct. 8, 2019

(54) METHODS FOR NON-INVASIVE DETECTION OF TRANSPLANT HEALTH OR REJECTION

(71) Applicant: MULTIPLICOM N.V., Niel (BE)

(72) Inventors: Dirk Goossens, Niel (BE); Joachim De Schrijver, Niel (BE); Jurgen Del Favero, Niel (BE)

(73) Assignee: MULTIPLICOM N.V., Niel (BE)

( * ) Notice: Subject to any disclaimer, the term of this patent is extended or adjusted under 35 U.S.C. 154(b) by 0 days.

(21) Appl. No.: 15/319,271

(22) PCT Filed: Jul. 3, 2015

(86) PCT No.: PCT/EP2015/065217
§ 371 (c)(1),
(2) Date: Dec. 15, 2016

(87) PCT Pub. No.: WO2016/001411
PCT Pub. Date: Jan. 7, 2016

(65) Prior Publication Data
US 2017/0137882 A1    May 18, 2017

(30) Foreign Application Priority Data
Jul. 3, 2014    (WO) ................. PCT/EP2014/064143

(51) Int. Cl.
*C12Q 1/68*    (2018.01)
*C12Q 1/6883*    (2018.01)
*C12Q 1/6809*    (2018.01)

(52) U.S. Cl.
CPC ......... *C12Q 1/6883* (2013.01); *C12Q 1/6809* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 5,496,699 | A | 3/1996 | Sorenson |
| 6,020,124 | A | 2/2000 | Sorenson |
| 6,251,638 | B1 | 6/2001 | Umansky et al. |
| 6,287,820 | B1 | 9/2001 | Umansky et al. |
| 6,492,144 | B1 | 12/2002 | Umansky et al. |
| 8,703,652 | B2 | 4/2014 | Quake et al. |
| 2010/0068711 | A1 | 3/2010 | Umansky et al. |
| 2016/0145682 | A1 | 5/2016 | Woodward et al. |

FOREIGN PATENT DOCUMENTS

| | | |
|---|---|---|
| EP | 0 655 090 A1 | 5/1995 |
| EP | 0 920 539 B9 | 3/2006 |
| EP | 1 634 966 A2 | 3/2006 |
| EP | 2 315 850 A0 | 1/2010 |
| EP | 2 216 416 A1 | 8/2010 |
| EP | 2 496 720 A0 | 9/2012 |
| WO | 9322456 A1 | 11/1993 |
| WO | 1996/40995 A1 | 12/1996 |
| WO | 1998/054364 A1 | 12/1998 |
| WO | 2010/009398 A1 | 1/2010 |
| WO | WO 2011/057061 A1 | 5/2011 |
| WO | 2013043922 A1 | 3/2013 |
| WO | 2013049892 A1 | 4/2013 |
| WO | 2013159035 A3 | 10/2013 |
| WO | WO 2013/159035 A2 | 10/2013 |

OTHER PUBLICATIONS

Beck et al., "Digital Droplet PCR for Rapid Quantification of Donor DNA in the Circulation of Transplant Recipients as a Potential Biomarker of Graft Injury," Clinical Chemistry, vol. 59, 2013, pp. 1732-1741.
Goossens et al., "Simultaneous Mutation and Copy Number Variation (CNV) Detection by Multiplex PCT-Based GS-FLX Sequencing," vol. 30, Mar. 2009, pp. 1-6.
International Search Report issued in International Parent Application No. PCT/EP2015/065217 dated Oct. 2, 2015.
Iwijin De Vlaminck et al., "Circulating Cell-Free DNA Enables Noninvasive Diagnosis of Heart Transplant Rejection," Science Translation Medicine, vol. 6, Jun. 2014, pp. 1-10.
Snyder et al., "Universal noninvasive detection of solid organ transplant rejection," PNAS, vol. 108, Apr. 2011, pp. 6229-6234.
Grskovic, Marica, et al., "Validation of a Clinical-Grade Assay to Measure Donor-Derived Cell-Free DNA in Solid Organ Transplant Recipients," The Journal of Molecular Diagnostics, vol. 18, No. 6, Nov. 2016, pp. 890-902, Elsevier Inc., from CareDx, Inc., Brisbane, CA; and the Advanced Heart Failure and Heart Transplantation Unit, Institute for Biomedical Research, University Hospital of Corunna, A. Coruna, Spain.

*Primary Examiner* — James Martinell
(74) *Attorney, Agent, or Firm* — Arent Fox LLP

(57) ABSTRACT

The present invention relates to the technical field of organ and tissue transplantation and specifically to methods allowing rejection of transplanted organs and tissues by a transplant patient. The present invention provides methods for non-invasive and ex vivo or in vitro detection of the presence or absence of transplant rejection, i.e. transplant health or rejection. The present methods allow for effective and continuous monitoring of transplant status with a minimal or absent discomfort for a transplant patient.

26 Claims, No Drawings

METHODS FOR NON-INVASIVE DETECTION OF TRANSPLANT HEALTH OR REJECTION

CROSS REFERENCE TO RELATED APPLICATION

This application is a 35 U.S.C. 371 National Phase of PCT Application No. PCT/EP2015/065217 filed Jul. 3, 2015, which claims priority to PCT Application No. PCT/EP2014/064143 filed Jul. 3, 2014. The disclosure of these prior applications are hereby incorporated by reference in their entirety.

The present invention relates to the technical field of organ and tissue transplantation and specifically to methods allowing detection of rejection of transplanted organs and tissues by a transplant patient or organ recipient/acceptor. The present invention provides methods for non-invasive, i.e. ex vivo or in vitro, detection of the presence or absence of transplant rejection, i.e. transplant health. The present methods allow for effective and continuous monitoring of transplant status with a minimal, or absent, discomfort for a transplant patent, i.e. an organ recipient or acceptor.

Organ transplantation is the transfer of an organ or tissue from a donor body or patient to a recipient body or patient for the purpose of replacing the recipient's damaged or absent organ or tissue. Transplants between two subjects of the same species, such as humans, are designated as allografts. Allografts can either be from a living or cadaveric source.

Examples of organs that can be transplanted are the heart, kidneys, liver, lungs, pancreas, intestine, and thymus. Examples of tissues include bones, tendons (both referred to as musculoskeletal grafts), cornea, skin, heart valves, nerves and veins. Worldwide, kidneys are the most commonly transplanted organs, followed by liver and heart. Cornea and musculoskeletal grafts are the most commonly transplanted tissues; these outnumber organ transplants by more than tenfold.

Transplantation medicine is one of the most challenging and complex areas of modern medicine. Some of the key areas for medical management are transplant rejection mainly due to an immune response against the transplanted organ. Such immune response often results transplant failure or transplant rejection and the need to immediately remove the transplanted organ or tissue from the recipient or acceptor. When possible, the chance of transplant rejection or failure can be minimized through serotyping in order to determine the most appropriate donor-recipient/acceptor match possibly in combination with the use of immunosuppressant drugs.

Kidney transplantation is generally considered for patients with end-stage renal disease (ESRD), regardless of the primary cause. Common diseases leading to ESRD include malignant hypertension, infections, diabetes mellitus, and focal segmental glomerulosclerosis; genetic causes include polycystic kidney disease, a number of inborn errors of metabolism, and autoimmune conditions such as lupus. Diabetes is the most common cause of kidney transplantation, accounting for approximately 25% of patients in the United States (US). The prevalence of ESRD in the US and developed nations is alarmingly high and dramatically increased compared to previous decades. Currently, haemodialysis, peritoneal dialysis and kidney transplantation are the only available therapies for ESRD. The majority of renal transplant recipients are on dialysis (peritoneal dialysis or hemofiltration) at the time of transplantation. However, individuals with chronic renal failure who have a living donor available may undergo pre-emptive transplantation before dialysis is needed.

Kidney transplantation is a life-extending procedure. Based on a three to four year follow-up period, the long term mortality for transplant patients was estimated to be 68% lower than that of patients not receiving a transplant. Kidney transplantation is typically classified as deceased-donor or living-donor transplantation depending on the source of the donor organ. Living-donor renal transplants are further characterized as genetically related (living-related) or non-related (living-unrelated) transplants, depending on whether a biological relationship is present between the donor and recipient. The average lifetime for a donated kidney is twelve to fifteen years.

The major barrier for organ transplantation between genetically non-identical individuals is the recipient's immune system, which will treat the transplanted kidney as an "invader" and immediately or chronically reject it. Therefore, it is essential to administer medication to suppress the immune system after transplantation. In the last two decades, the available number of immunosuppressive agents has increased greatly. Agents can be used as induction therapy (at the time of transplant), as maintenance therapy (to prevent rejection of the allograft), or for treatment of acute rejection.

Recommendations for immunosuppressive medications are necessarily complex, because combinations of multiple classes of immunosuppressive drugs are used and because the choice among different regimens are determined by the trade-offs between benefits and harm. Typically, a greater degree of immunosuppression may reduce the risk of rejection, but may also increase the risk of infection and cancer. Standard post transplantation therapy consists of a calcineurin inhibitor, antiproliferative agents, and corticosteroids. The calcineurin inhibitors, cyclosporine and tacrolimus, are a mainstay of maintenance immunosuppression. They inhibit IL-2 transcription, and suppress effector T-cells. Both have similar side effects, such as new-onset diabetes after transplantation, hyperlipidemias, hypertension, osteopenia and a decreased glomerular filtration rate. They both also cause significant nephrotoxicity.

The antiproliferative agents, mycophenolate mofetil, mycophenolic acid, and azathioprine, often cause diarrhea and gastrointestinal discomfort and may be associated with an increased risk of tissue-invasive CMV. They are used in combination with aforementioned drugs for maintenance of immunosuppression. Corticosteroids have traditionally been a mainstay of maintenance immunosuppression in kidney transplant recipients. Prednisolone suppresses the immune system, but its long-term use at high doses causes a multitude of side effects, including glucose intolerance and diabetes, weight gain, osteoporosis, muscle weakness, hypercholesterolemia, and cataract formation. Prednisolone alone is usually inadequate to prevent rejection of a transplanted kidney.

Kidney transplantation is the treatment of choice for patients with ESRD, improving survival and quality of life and lowering costs of dialysis as stated above. However, the alloimmune response induced by transplantation from a donor who differs genetically from the kidney recipient remains a major obstacle to graft success. Recipient factors, donor factors, and donor/recipient compatibility all influence the long-term graft survival.

Superior graft survival has been established in recipients/donors who are younger, have spent less time on dialysis. Also race and ethnicity may affect graft survival. Kidneys from living (related or non-related) donors survive longer on average than deceased donor kidneys. Pre-sensitized patients have developed antibodies against histocompatibility antigens as a result of blood transfusions, pregnancy, or prior failed transplant. These antibodies are called panel reactive antibodies (PRA). Low PRA levels indicate a greater chance of graft success. Finally, factors of donor and recipient compatibility also affect outcomes: better HLA matching, CMV serologic status matching and equivalent donor/recipient BMI all have positive effects on long-term graft survival.

Worldwide, approximately 63.000 patients yearly receive a kidney transplant. In Europe in 2013, a total of 4.400 kidney transplants were performed of which 3000 from deceased donors and 1400 patients from living donors.

Since the demand for transplant kidneys far exceeds the supply of available organs, there is a long waiting list. The median time to transplant for new candidates ranges between 1100 to 1200 days. In an attempt to shorten the waiting list, donor organs have been expanded to 'marginal' kidneys. These so called expanded criteria donor (ECD) kidneys are derived from normally aged 60 years or older, or over 50 years with at least two of the following conditions: hypertension history, serum creatinine >1.5 mg/dl or cause of death from cerebrovascular accident.

The risk of graft loss has traditionally been divided into an early, high-risk period and a later period of constant low risk. Short-term graft survival risks include delayed allograft function, HLA antibodies, type of donor kidney (living donor vs. deceased, expanded donor criteria), donor illness (cardiovascular, donor age (higher risk >60 y)), and other factors. Long-term risk factors are an increased serum creatinine concentration, proteinuria, and increased pulse pressure.

Chronic rejection and allograft loss are more likely to develop in patients with a history of acute rejection, a greater degree of HLA mismatching, infection, and/or inadequate immunosuppressive therapy. Through the use of immunosuppression and better immunologic matching of recipients with donors, the overall risk of acute rejection within 1 year after transplantation is now approximately 15%.

It is important to diagnose a rejection as early as possible in order to adapt the treatment to save the allograft. Therefore, there is a critical need for non-invasive detection and prediction methods that can be used in the early detection of allograft rejection. The current diagnostic criteria of transplant rejection will be discussed below.

Transplanted patients are very closely monitored in the first three months after transplantation through extensive clinical and laboratory based monitoring to detect signs of rejection. Currently, a rejection is diagnosed based on both measuring biochemical parameters with a low diagnostic specificity, such as serum creatinine, and the pathological findings on a renal biopsy. A rise in serum creatinine points to rejection; although a subclinical rejection may be apparent only after kidney biopsy and can, in absence of renal dysfunction, damage the allograft. Rejection can be hyper acute (within minutes after transplantation), acute (within days to weeks), late acute (after 3 months), or chronic (months to years after transplantation).

A biopsy is taken when an allograft rejection is suspected, based on a rise in serum creatinine. However, a number of factors, such as the original quality of the donated organ, ischemia, acute and subclinical rejection, chronic humoral rejection, and effect of CNI-induced nephrotoxicity, will adversely affect renal structure, causing early tubular atrophy and interstitial fibrosis, followed by arteriolar hyalinosis, arteriosclerosis, and glomerular sclerosis, before creatinine levels start to rise.

Consequently, there is not a reliable correlation between serum creatinine and kidney damage. At the point that the level of serum creatinine goes up, the glomerular filtration rate may already be severely reduced. For this reason, the serum creatinine test isn't useful in diagnosing early-stage kidney damage. In addition, few well performed studies are available on the sensitivity and specificity of serum creatinine concentrations after kidney transplantation. Today, biopsy analysis from the kidney allograft remains the golden standard to diagnose rejection and other graft-associated pathologies.

Although kidney allograft biopsies allow for diagnosis of graft pathology, it is unpractical, labor-intensive, costly and not without risk for the patient, i.e. the recipient or acceptor.

Therefore, there is a critical need in the art for non-invasive detection and prediction methods that can be used in the early detection of allograft rejection allowing frequent monitoring of the renal graft without any morbidity to the patient.

Given the low sensitivity of the existing biochemical biomarkers and the risk and cost associated with renal biopsies as allograft monitoring tools, it is clear that novel, risk free and affordable biomarkers are needed to monitor allograft health after transplantation.

A class of biomarkers that may fulfil these requirements were discovered more than 60 years ago with the observation that the bloodstream of every individual contains (circulating) cell free DNA or (c)cfDNA and that increased levels of cfDNA appear to be associated with a number of clinical disorders.

Over the past 15 years, there has been increasing interest in the use of cfDNA in plasma and urine samples for molecular diagnostics, especially for cancer detection and prenatal diagnosis. Typically, cfDNA has a size range between 50 and 200 bp as a result of DNA nuclease digestion of the released DNA. In 1998, it was shown that donor-derived DNA sequences were present in the plasma of transplant recipients. This group further showed that different transplanted organs e.g., the heart, liver, and kidney appeared to release different amounts of DNA into the plasma, probably related to the size of the organ.

As cell death is generally accepted to be an important reason for the release of DNA into the plasma, it was further hypothesized that the measurement of donor-derived DNA in the plasma of transplant recipients might be used for monitoring graft rejection because donor-derived cfDNA was detected in the recipient's blood and urine after solid organ allograft transplantation. It has been shown that urinary cfDNA after renal transplantation has patient specific thresholds, reflecting the apoptotic injury load of the donor organ. Serial monitoring of urinary cfDNA can thus be a sensitive biomarker of acute injury of the donor organ.

To date, most experiments were performed in female patients transplanted with a male donor organ. As such, the presence of donor-derived cfDNA was measured by amplification of a Y-linked gene (e.g. TSPY1, SRY). This gender analysis prevents the wide-spread use of cfDNA as a diagnostic tool, because female recipients of male donor organs represent less than a quarter of all transplant procedures.

A qPCR based test that specifically detects polymorphisms in the HLA region of the donor derived HLA alleles was shown to enable donor derived cfDNA detection. Although this strategy has broader population coverage than the above-mentioned sex-mismatched strategy, it nonetheless requires specific assays to be designed for each donor-recipient pair.

The recent availability of single molecule counting techniques allows detection of donor kidney derived cfDNA. Hereto, informative SNPs are required, i.e. SNPs that are homozygous in the recipient and either heterozygous or homozygous for the other allele in the donor. Digital droplet PCR and MPS are both single molecule counting methods, which allow quantification of nucleic acids by counting molecules and have superior analytical precision compared to conventional PCR or qPCR based detection methods.

Digital droplet PCR refers to the performance of multiple PCRs in parallel in which each PCR typically contains either a single or no target molecule. Counting the number of positive reactions at the end of the amplification allows determining the number of input target molecules. Recently, a novel digital droplet PCR method was described to quantify donor DNA in the recipient's blood. Hereto, a set of 41 SNP assays (minor allele frequency [MAF] >40%), was used which first were analyzed on the genomic DNA of the recipient to determine homozygous SNPs. All homozygous SNPs were subsequently used to genotype the recipient's cfDNA enabling the measurement of the donor cfDNA fraction by using a hydrolysis based SNP assay in combination with digital droplet PCR.

Analysis of 27 cfDNA samples showed that donor organ derived cfDNA was successfully detected in all patients and showed that the number of obtained informative SNPs ranged between 2 and 9 with an average of 3 informative SNPs per patient.

For digital PCR, quantitative precision improves with increasing number of PCR analyses performed. Therefore, several thousands digital PCRs need to be performed, requiring the use of automated platforms. Such automated platforms using microfluidics are available (e.g. Fluidigm) but are expensive.

Massively parallel sequencers allow analysis of nucleotide sequences of millions to billions of DNA molecules in each run. Therefore, in addition to the identity, a frequency distribution of the DNA molecules in the analyzed sample can be obtained. Since cfDNA in plasma is fragmented in nature it can be used directly to identify the origin of each DNA molecule and determine the proportion of molecules derived from the donor organ.

A paper published in 2011 showed that universal non-invasive monitoring of organ transplant health can be performed using MPS on plasma derived cfDNA from hart transplant patients. Hereto, sequencing adaptors were ligated to the cfDNA which was subsequently sequenced on an Illumnia GAII platform generating 15 to 20 million reads per sample.

The resulting 36 bp reads were mapped to the human reference genome and unique reads spanning a SNP were used to calculate the donor derived cfDNA fraction taken into consideration the a priori determined genotypes on the donor's and recipient's genomic DNA using a SNP array. The donor DNA percentage was calculated by taking twice the number of donor heterozygous read calls plus the number of donor homozygous read calls over the total number of donor and recipient read calls. On average about 0.001% of the total number of generated MPS reads can be used to calculate the SNP based donor derived cfDNA fraction.

Using the above described method, the authors demonstrated that donor-derived cfDNA exists in the plasma of organ transplant recipients, and that elevated levels of donor DNA can be used as an indication of organ rejection. Their data establish unambiguously that donor-specific DNA is present in the plasma of heart transplant recipients and that the level of donor specific cfDNA represents mean values of 1% of the total cfDNA fraction. During organ rejection, however, the level of donor DNA signal rises with values increasing up to 5% of the total cell-free DNA.

The main advantage of this method is that it can be used for all donor-recipient pairs. Thus, this strategy may have a more general applicability than previous approaches based on Y-chromosomal markers and genetic markers in the HLA region. The potential disadvantage of this approach is costliness MPS and the complexity of the subsequent bioinformatics analysis compared with conventional PCR-based detection strategies. The cost issue is further compounded by the fact that testing at multiple time points may be needed for a particular transplant recipient for monitoring purposes. The costs associated with MPS are falling rapidly, however, and it is likely that the cost will no longer be a substantial issue in a few years time.

Nevertheless, since a substantial number of sequences need to be generated of which only a small fraction is used to determine the health of a transplant organ, this method will hamper simultaneous analysis of large numbers of samples and/or will require high end, expensive, sequencers resulting in substantial investment in equipment and specialized personnel to efficiently perform the required number of analyses.

Considering the above, it is an object of the present invention, amongst objects, to at least partially obviate the above problems associated with organ and tissue transplantation.

The above object of the present invention, amongst other objects, is met by methods for non-invasive detection of transplant health or rejection in a recipient of a tissue or organ from a donor as outlined in the appended claims.

Specifically, the above object, amongst other objects is met by the present invention by methods for non-invasive detection of transplant health or rejection in a recipient of a tissue or organ from a donor, the method comprises the steps of:
   a) amplifying at least 250 amplicons by nucleic acid amplification wherein each amplicon comprises a Single Nucleotide Polymorphism (SNP) thereby providing amplified amplicons wherein said amplification is performed on at least one sample A of said acceptor and at least one sample of said donor or, in the alternative, on at least one sample A of said acceptor;
   b) determining the nucleic acid sequence of said amplified amplicons from said at least one sample A of said acceptor and determining the nucleic acid sequence of said amplified amplicons from said at least one sample of said donor or, in the alternative, determining the nucleic acid sequences of said amplified amplicons of said acceptor and said donor from said at least one sample A and determining donor discriminating amplicons;
   c) determining the presence of donor discriminating amplicons in a sample B of said recipient by nucleic acid amplification of cell free DNA (cfDNA) wherein the presence or amount of amplified donor discriminating amplicons in said sample B is indicative for transplant health or rejection.

According to a preferred embodiment, the present amplification in step (a) is a multiplex Polymerase Chain Reaction (PCR).

According to another preferred embodiment, the present nucleic acid amplification in step (c) is a multiplex Polymerase Chain Reaction (PCR).

According to yet another preferred embodiment of the present method, the present amplification in step (a) is a multiplex Polymerase Chain Reaction (PCR) and the present nucleic acid amplification in step (c) is a multiplex Polymerase Chain Reaction (PCR).

According to an especially preferred embodiment of the present method determining the nucleic acid sequence in step (b) is performed using massively parallel sequencing; or determining the presence of donor discriminating amplicons in step (c) is performed using massively parallel sequencing; or determining the nucleic acid sequence in step (b) is performed using massively parallel sequencing and determining the presence of donor discriminating amplicons in step (c) is performed using massively parallel sequencing.

According to another especially preferred embodiment, step (c) of the present method further comprises that the amount of donor discriminating amplicons is determined, wherein the amount is indicative for detection of transplant health or rejection.

The present method is preferably used for assaying transplant health or rejection of transplants selected from the group consisting of heart, blood vessel, gland, esophagus, stomach, liver, gallbladder, pancreas, intestines, colon, rectum, endocrine gland, kidney, ureters, bladder, spleen, thymus, spinal cord, ovaries, uterus, mammary glands, testes, vas deferens, seminal vesicles, prostate, pharynx, larynx, trachea, bronchi, lungs, diaphragm, bone, cartilage, ligament, tendon and parts and tissues thereof.

According to still another preferred embodiment of the present invention, the present at least one sample of said donor is a biopsy of said transplanted tissue or organ.

According to a more preferred embodiment of the present method, the present sample B is derived from blood, urine, faces or sputum, such as whole blood, serum or plasma.

The present method is especially suitable for detecting acute or chronic transplant rejection, such as transplant rejection caused by graft-versus-host disease.

According to a most preferred embodiment, present step (c) is repeated at different time-points after receiving said tissue or organ from said donor thereby providing continuous monitoring of transplant health or rejection.

The present invention will be further illustrated in the following example outlined a most preferred embodiment of the present invention.

EXAMPLE

The NIOTT MASTR assay was being used throughout this example to exemplify the concept for targeted, multiplex amplification of SNP containing amplicons in combination with MPS to enable monitoring of the donor cfDNA fraction in blood and urine derived from recipient cfDNA.

The design of the NIOTT MASTR assay is based on the current NIAT MASTR assay, which comprises 6.592 SNP containing amplicons. The NIAT MASTR assays was used to analyze >200 blood derived cfDNA samples from pregnant women and thus generated a wealth of information on the performance of each of the amplicons present in the assay. Based on this information a set of 1000 SNP containing amplicons was selected to establish the NIOTT MASTR assay. The minimal amplicon selection criteria were:

Amplicons with least amplification variation;
Amplicons with most efficient amplification;
Amplicons devoid of allele specific amplification bias.

The optimization steps were based on the reiterative adjustment of individual primer concentrations in the multiplex PCR assay. The NIOTT MASTR optimization process consists of the following steps:

1. Add all 2000 primers to one vial at the same concentration.
2. Verify amplification efficiency of each amplicons by MiSeq based MPS on 8 DNA samples.
3. Based on the resulting read counts for each amplicon, increase primer concentration of amplicons showing less efficient amplification.
4. Reiterate steps 2 and 3 until the read counts of all amplicons are within one standard deviation.

Based on the individual primer pair concentrations obtained from the optimization phase, two independent NIOTT MASTR assay batches were produced and evaluated by MiSeq based MPS on 4 DNA samples. One batch was produced for 500 NIOTT tests and a second batch was produced to deliver 2000 NIOTT tests.

In order to take full advantage of the power of targeted amplification with the NIOTT assay in combination with MPS, it is required to obtain the genotypes of both the donor and the recipient. Hereto, blood derived genomic DNA was used as template DNA for amplification with the NIOTT MASTR assay. The resulting NIOTT amplification product was subsequently sequenced on a MiSeq at low amplicon coverage. Based on experience with a germ line MASTR assay it was shown that an average amplicon coverage of 100 read counts is sufficient to unambiguously determine heterozygous variants. Therefore, to generate the donor and recipient genotypes approximately 100.000 reads per sample were required, corresponding to 0.5% of the capacity of a MiSeq run with the current sequencing chemistry.

For each patient, urine and blood samples were collected at ten fixed time points at days 1, 3, 7, 14, 21, 28, 42, 56, 70 and 90 post-transplantation. This will result in total of 1400 samples; 700 blood samples and 700 urine samples. cfDNA isolation, NIOTT amplification and MPS analysis of all these samples is for budgetary and logistics reasons not feasible. Therefore, a pilot study was performed to evaluate the best cfDNA source, i.e. cfDNA derived from urine or from blood. The best cfDNA source is defined as the source that provides the highest total cfDNA yield and the highest donor cfDNA fraction.

For this pilot experiment, from urine and blood samples from 35 transplant patients cfDNA was extracted, NIOTT amplified and MPS analyzed for all ten time points, resulting in 700 cfDNA samples. The total cfDNA yield from each cfDNA extraction was spectrophotometric determined. Subsequent, MPS data analysis enabled quantification of the donor cfDNA fraction. The results from the pilot experiment enabled determining which cfDNA source is significantly better performing. In case cfDNA extraction from blood and urine are equivalent in yield and donor fraction a decision for the preferred source is to be made based on economical and clinical considerations. In both cases this will lead to the decision to select one of both cfDNA sources for the NIOTT proof of concept on the remaining transplant patients.

After selection of the best cfDNA source, the sampling and cfDNA extraction procedure for newly included patients and/or samples were restricted to the best cfDNA source only.

It is essential to determine the post transplantation evolution of the donor cfDNA fraction since no published study evaluated this in detail. The few MPS based studies performed show that the donor cfDNA fraction in a healthy transplant is below or at 1% of the total cfDNA fraction. Furthermore, a recent study showed that the donor cfDNA fraction can be very high, up to 90% of the total cfDNA fraction, in the first day post transplantation dropping sharply to baseline level after a few days.

To confirm this observation the data generated from all sample time points obtained from the 35 patients was used. The results of this analysis had three main consequences:
  (i) if the presence of a high donor cfDNA fraction in the first days post transplantation can be confirmed than this allows determination of the donor genotype directly from the recipient sample post transplantation. The consequence being that it is no longer required to obtain a tissue samples from the kidney donor which can be difficult in cases when the donor is deceased;
  (ii) if a high donor cfDNA fraction is present in the first days post transplantation than this will hamper identification of acute kidney rejection which typically occur in the first few days post transplantation;
  (iii) the longitudinal analysis of the 35 patients will allow determination of the baseline cfDNA fraction per individual patient and at the same time will allow determination of the baseline variance between transplant patients.

To substantiate the results obtained, all transplant patients were used. Hereto, the cfDNA from the best source of the remaining 35 patients was used to obtain NIOTT data resulting in the generation of 350 MPS datasets.

All participating patients were subjected to the standard of care monitoring tools. To evaluate if the NIOTT/MPS method can serve as an universal technology for the early detection of kidney rejection, it is essential to show that kidney rejection can be detected substantially earlier than with the conventional monitor tools. Hereto, the urine or blood samples for all ten time points of patients that show signs of kidney rejection based on the current monitoring tools, were used to determine the donor cfDNA fraction with the NIOTT/MPS technology. The resulting data will allow determining the effectiveness of cfDNA as biomarker for the pre-clinical detection of kidney rejection. Also, it will allow determining the sensitivity and specificity of the NIOTT/MPS based procedure in predicting kidney rejection.

Sequencing was performed on MiSeq and NextSeq500 Illumina sequencers. MiSeq based sequencing will be used to generate the genotypes of the donor and recipient genomic DNA. A total of 140 samples was sequenced to generate all genotypes which corresponds to 1 MiSeq run using the V3 sequencing chemistry. Also, MiSeq capacity is required to optimize and produce the NIOTT assay as described. A total of 6 MiSeq runs was required to successfully perform this task.

The 1150 cfDNA samples that require sequencing were sequenced on the NextSeq 500. Assuming $2 \times 10^6$ reads per samples and a NextSeq 500 run capacity of $400 \times 10^6$ reads, a total of 6 NextSeq 500 runs are required.

To allow cross MPS platform validation a set-up of 100 samples were run on both the MiSeq and NextSeq 500 sequencers. Since the run capacity per MiSeq is $25 \times 10^6$ reads and $2 \times 10^6$ per sample this will require 8 MiSeq runs.

Based on current experience with the NIAT assay in combination with Illumina sequencing, the following workflow was utilized to determine variant frequencies of data generated with the NIOTT assay:
  1) Trim adapter sequence: The NIOTT amplicons are between 65 and 85 bp long. Due to the read length on MiSeq or HiSeq (typically $1 \times 75$ bp), adapter sequences are often partially present at the 3'-end of the sequenced reads. These adapter sequences are removed using cutadapt, resulting in better alignment results and allowing primer dimer sequences to be removed.
  2) Remove primer dimer sequences: After adapters are trimmed, sequenced reads should be at least 65 bp long (the minimal amplicon size). Sequences shorter than 65 bp are considered as primer-dimer sequences and are discarded from the dataset. The NIAT assay has shown that the fraction of primer dimer sequences in the total dataset acts as an important sample quality parameter reflecting input DNA concentration and DNA fragmentation.
  3) Align reads to the NIOTT reference set, using Bowtie2.
  4) Call variants: Each of the amplicons is designed to contain one known SNP which is roughly located in the middle of the amplicon. Variants within amplicons on positions other than the designed polymorphic site are discarded. This approach strongly simplifies data analysis and allows sequencing errors to be separated from genuine variants, even at low variant frequencies.

Once variants and variant frequencies were determined, the donor cfDNA fraction was calculated. Following variant frequency determination, there are two options, depending on availability of data and the research question (longitudinal study or single time point analysis).
  1) Genotype of both donor and recipient are available: Observed variant frequencies in cfDNA are matched to donor and recipient genotype using a maximum likelihood approach where the donor cfDNA fraction is the variable of interest. The donor cfDNA fraction is computationally varied from 0 to 100%. As the genotype of both donor and acceptor are known, expected cfDNA mixtures (a set of SNP frequencies) can be calculated for each of these cfDNA fractions. The cfDNA fraction of the expected cfDNA mixture best matching the observed cfDNA mixture is the estimated cfDNA fraction.
  2) Genotype of both donor and acceptor are not available: since the donor cfDNA fractions in a healthy kidney transplant patient are typically very low, SNPs present uniquely in the donor (either heterozygous or homozygous), can easily be discriminated from recipient SNPs. The evolution of these SNPs frequencies through time can be used to calculate the evolution of donor cfDNA fraction in a longitudinal study.

Many different samples will be sequenced after applying the NIOTT assay. Some of these samples will be involved in a longitudinal analysis. Furthermore, MPS generates a vast amount of data, increasing the need for a structured approach regarding data handling, storage and annotation. To avoid human interaction, inherent introduction of human error and to reduce the risk of losing or switching datasets, all data will be maintained in a dedicated database system.

The invention claimed is:

1. A method for amplifying at least one sample from a recipient of a tissue or organ from a donor, comprising
  a) amplifying at least 250 amplicons by nucleic acid amplification wherein each amplicon comprises a Single Nucleotide Polymorphism (SNP) thereby providing amplified amplicons wherein said amplification is performed on:
    i) at least one sample A of said recipient and at least one sample of said donor, or
    ii) at least one sample A of said recipient;
  b) determining the nucleic acid sequence of said amplified amplicons from said at least one sample A of said recipient and determining the nucleic acid sequence of said amplified amplicons from said at least one sample of said donor or determining the nucleic acid sequences of said amplified amplicons of said recipient and said donor from said at least one sample A thereby determining donor discriminating amplicons; and c) amplifying cell free DNA (cfDNA) from a sample B of said recipient to determine the presence of donor derived alleles.

2. The method according to claim 1, wherein said amplification in step (a) comprises a multiplex Polymerase Chain Reaction (PCR).

3. The method according to claim 1, wherein said nucleic acid amplification in step (c) comprises a multiplex Polymerase Chain Reaction (PCR).

4. The method according to claim 1, wherein said determining the nucleic acid sequence of said amplified amplicons from said at least one sample A of said recipient and determining the nucleic acid sequence of said amplified amplicons from said at least one sample of said donor in step (b) is performed using massively parallel sequencing.

5. The method according to claim 1, wherein said determining the nucleic acid sequences of said amplified amplicons of said recipient and said donor from said at least one sample A in step (b) is performed using massively parallel sequencing.

6. The method according to claim 1, further comprising, in step (c), determining the amount of donor derived alleles, said amount is indicative for detection of transplant health or rejection.

7. The method according to claim 1, wherein said tissue or organ is selected from the group consisting of heart, blood vessel, gland, esophagus, stomach, liver, gallbladder, pancreas, intestines, colon, rectum, endocrine gland, kidney, ureters, bladder, spleen, thymus, spinal cord, ovaries, uterus, mammary glands, testes, vas deferens, seminal vesicles, prostate, pharynx, larynx, trachea, bronchi, lungs, diaphragm, bone, cartilage, ligament, tendon and parts and tissues thereof.

8. The method according to claim 1, wherein said at least one sample of said donor is a biopsy of said transplanted tissue or organ.

9. The method according to claim 1, wherein said sample B is derived from blood, urine, or sputum.

10. The method according to claim 1, wherein said sample is whole blood, serum or plasma.

11. The method according to claim 1, further comprising repeating step (c) at different time-points after receiving said tissue or organ from said donor.

12. The method of claim 1, wherein the 250 amplicons are selected based on amplicons with the least amplification variation, amplicons with the most efficient amplification, and amplicons devoid of allele specific amplification bias.

13. The method of claim 1, wherein said at least 250 amplicons is at least 500, at least 1000, at least 1500 or at least 2000 amplicons.

14. A method for producing an amplification product from a recipient of a tissue or organ from a donor, comprising a) amplifying at least 250 amplicons by nucleic acid amplification wherein each amplicon comprises a Single Nucleotide Polymorphism (SNP) thereby providing amplified amplicons wherein said amplification is performed on:

i) at least one sample A of said recipient and at least one sample of said donor, or ii) at least one sample A of said recipient;

b) determining the nucleic acid sequence of said amplified amplicons from said at least one sample A of said recipient and determining the nucleic acid sequence of said amplified amplicons from said at least one sample of said donor or determining the nucleic acid sequences of said amplified amplicons of said recipient and said donor from said at least one sample A thereby determining donor discriminating amplicons; and c) amplifying cell free DNA (cfDNA) from a sample B of said recipient to determine the presence of donor derived alleles.

15. The method of claim 14, wherein the 250 amplicons are selected based on amplicons with the least amplification variation, amplicons with the most efficient amplification, and amplicons devoid of allele specific amplification bias.

16. The method of claim 14, wherein said at least 250 amplicons is at least 500, at least 1000, at least 1500 or at least 2000 amplicons.

17. The method according to claim 14, wherein said amplification in step (a) comprises a multiplex Polymerase Chain Reaction (PCR).

18. The method according to claim 14, wherein said nucleic acid amplification in step (c) comprises a multiplex Polymerase Chain Reaction (PCR).

19. The method according to claim 14, wherein said determining the nucleic acid sequence of said amplified amplicons from said at least one sample A of said recipient and determining the nucleic acid sequence of said amplified amplicons from said at least one sample of said donor in step (b) is performed using massively parallel sequencing.

20. The method according to claim 14, wherein said determining the nucleic acid sequences of said amplified amplicons of said recipient and said donor from said at least one sample A in step (b) is performed using massively parallel sequencing.

21. The method according to claim 14, further comprising, in step (c), determining the amount of donor derived alleles, said amount is indicative for detection of transplant health or rejection.

22. The method according to claim 14, wherein said tissue or organ is selected from the group consisting of heart, blood vessel, gland, esophagus, stomach, liver, gallbladder, pancreas, intestines, colon, rectum, endocrine gland, kidney, ureters, bladder, spleen, thymus, spinal cord, ovaries, uterus, mammary glands, testes, vas deferens, seminal vesicles, prostate, pharynx, larynx, trachea, bronchi, lungs, diaphragm, bone, cartilage, ligament, tendon and parts and tissues thereof.

23. The method according to claim 14, wherein said at least one sample of said donor is a biopsy of said transplanted tissue or organ.

24. The method according to claim 14, wherein said sample B is derived from blood, urine, or sputum.

25. The method according to claim 14, wherein said sample is whole blood, serum or plasma.

26. The method according to claim 14, further comprising repeating step (c) at different time-points after receiving said tissue or organ from said donor.

* * * * *

UNITED STATES PATENT AND TRADEMARK OFFICE
CERTIFICATE OF CORRECTION

PATENT NO. : 10,435,750 B2  
APPLICATION NO. : 15/319271  
DATED : October 8, 2019  
INVENTOR(S) : Dirk Goossens et al.

Page 1 of 1

It is certified that error appears in the above-identified patent and that said Letters Patent is hereby corrected as shown below:

In the Specification

Column 1, Line 23, delete "patent," and insert -- patient, --, therefor.

Column 5, Line 48, delete "hart" and insert -- heart --, therefor.

Column 5, Line 51, delete "Illumnia" and insert -- Illumina --, therefor.

Signed and Sealed this  
Thirtieth Day of June, 2020

Andrei Iancu  
*Director of the United States Patent and Trademark Office*